US00PP14830P3

(12) United States Plant Patent
Hasegawa

(10) Patent No.: US PP14,830 P3
(45) Date of Patent: May 25, 2004

(54) CARNATION PLANT NAMED 'CFPC YELLOW LACY'

(50) Latin Name: *Dianthus caryophyllus*
Varietal Denomination: CFPC Yellow Lacy

(75) Inventor: Oscar T. Hasegawa, Salinas, CA (US)

(73) Assignee: California Florida Plant Company, L.P., Salinas, CA (US)

( * ) Notice: Subject to any disclaimer, the term of this patent is extended or adjusted under 35 U.S.C. 154(b) by 0 days.

(21) Appl. No.: 10/208,118

(22) Filed: Jul. 29, 2002

(65) Prior Publication Data

US 2004/0019941 P1 Jan. 29, 2004

(51) Int. Cl.[7] ..... A01H 5/00
(52) U.S. Cl. ..... Plt./273
(58) Field of Search ..... Plt./275

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new variety of carnation plant producing attractive yellow flowers.

1 Drawing Sheet

Classification: The present invention relates to a new Hybrid *Dianthus caryophyllus* plant.

Variety denomination: The new plant has the varietal denomination 'CFPC Yellow Lacy'.

BACKGROUND OF THE INVENTION

The present invention relates to a new and distinct variety of carnation plant which was discovered by me as a naturally occurring sport in a controlled planting of 'CFPC Lacy' (U.S. Plant Pat. No. 11,884). The varietal denomination of the new variety is 'CFPC Yellow Lacy'.

SUMMARY OF THE INVENTION

Among the novel characteristics possessed by the new variety which distinguish it from other varieties of which I am aware, are its attractive yellow flowers which retain color without fading. When grown in a greenhouse in Salinas, Calif., in 4½ inch plastic pots, pinched plants are about 7 inches tall and about 7 inches in diameter. Flower diameter averages about 2 inches with a crown of about 1 inch (average). Foliage is about 3¼ inches long and about 7/16 inch wide at its widest point.

Asexual reproduction by propagation by cuttings of the new variety as performed in Salinas, Calif., shows that the foregoing and other distinguishing characteristics come true to form and are established and transmitted through succeeding propagation.

COMPARISON WITH PARENT

The new variety has yellow flowers whereas 'CFPC Lacy' has yellow picotee purple flowers.

BRIEF DESCRIPTION OF ILLUSTRATION

The accompanying illustration shows a typical specimen of the vegetative growth and flowers of the new variety depicted in color as nearly true as it is reasonably possible to make the same in color illustration of this character.

DESCRIPTION OF THE NEW VARIETY

The following is a detailed description of the new variety, with color terminology in accordance with The Royal Horticultural Society Colour Chart (R.H.S.C.C.). The terminology used in color description herein refers to plate numbers in the aforementioned color chart. Phenotypical expression may vary depending upon varying environmental, seasonal and cultural conditions.

The information provided herein is based on observations of 110-day-old plants grown inside commercial greenhouses at Salinas, Calif. The height of plant and flower and foliage size are established as an average using standard commercial cultural practices.

Classification:
- *Botanical.*—Hybrid *Dianthus caryophyllus.*
- *Commercial.*—Carnation, standard disbud, type, suitable for production as a pot spray.

Plant:
- *Height.*—About 7 inches.
- *Form.*—Herbaceous.
- *Growing habit.*—Semi-upright.
- *Blooming habit.*—As a spray (pot).
- *Blooming season.*—Year round.
- *Rooting time/habit.*—About 18 days.
- *Breaking action.*—Averages about 15 breaks per plant.
- *Mutation prone.*—No.
- *Disease resistance.*—Good, resistence to soil — borne diseases such as *Fusarium oxysporum,* and *F. graminearum* and root-rots such as damping off, water molds and the like as is typical of carnations.
- *Temperature tolerance.*—Wide range.

Foliage (base of plant):
- *Color.*—Upper side: Near 136B. Lower side: Near 137B.
- *Size.*—About 3¼ inches long and about 7/16 inch wide.
- *Leaf base and apex.*—Leaf base edge smooth, color near 145D; leaf apex edge smooth, color near 136B.
- *Quantity.*—Numerous.
- *Shape.*—Lanceolate.
- *Texture.*—Smooth.

*Ribs.*—Central keel.
*Arrangement.*—Bi-lateral along stem.
*Stem.*—Color: Near 135A at maturity. Size: Stem diameter about ⅛ inch.
*Bud.*—Shape: Ovoid. Color: Near 138C. Length: About 1 inch. Diameter: About 7/16 inch.
*Calyx.*—Sepals: About 5. Length: About ¼ inch. Width: About ¼ inch. Color Outside: Near 138C. Inside: Near 147C.

Bloom:
*Shape.*—Rounded.
*Size.*—Diameter: About 2 inches. Depth: About 1 inch.
*Borne.*—As a spray.
*Color.*—General tonality: Yellow with picotee faint pink. Upper side: Near 8C. Lower side: Near 8D. Center: Near 8C. Outer petals: Near 56C.
*Permanence.*—Dry up on receptacle.
*Keeping quality.*—Very good, about 3 weeks.
*Fragrance.*—Slight.

Petalage:
*Quantity.*—Average between 25 to 26.
*Outer petal size.*—Length: About 1 9/16 inches. Width: About 1 inch.
*Central petal size.*—Length: About 1½ inches. Width: About ¾ inch.
*Texture.*—Smooth.
*Appearance.*—Shiny, petal edge finely serrated, color near 56C in continuous picotee pattern of about 1/32 inch width.
*Form.*—Fan shaped.

Reproductive organs:
*Stamen.*—None.
*Anthers.*—None.
*Filaments.*—None.
*Pistil.*—1. Length: About 15/16 inch. Color: Whiter than 155D.
*Stigma.*—2 (bi-lobed). Color: Whiter than 155D.
*Fertility.*—Male: Sterile. Female: Good.
*Ovary.*—Shape: Conical. Color Base: Near 155D. Body: Near 147C. Apex: Near 147C.
*Fruit.*—No fruit or seed produced.

I claim:

1. A new and distinct carnation plant of the variety substantially as herein shown and described.

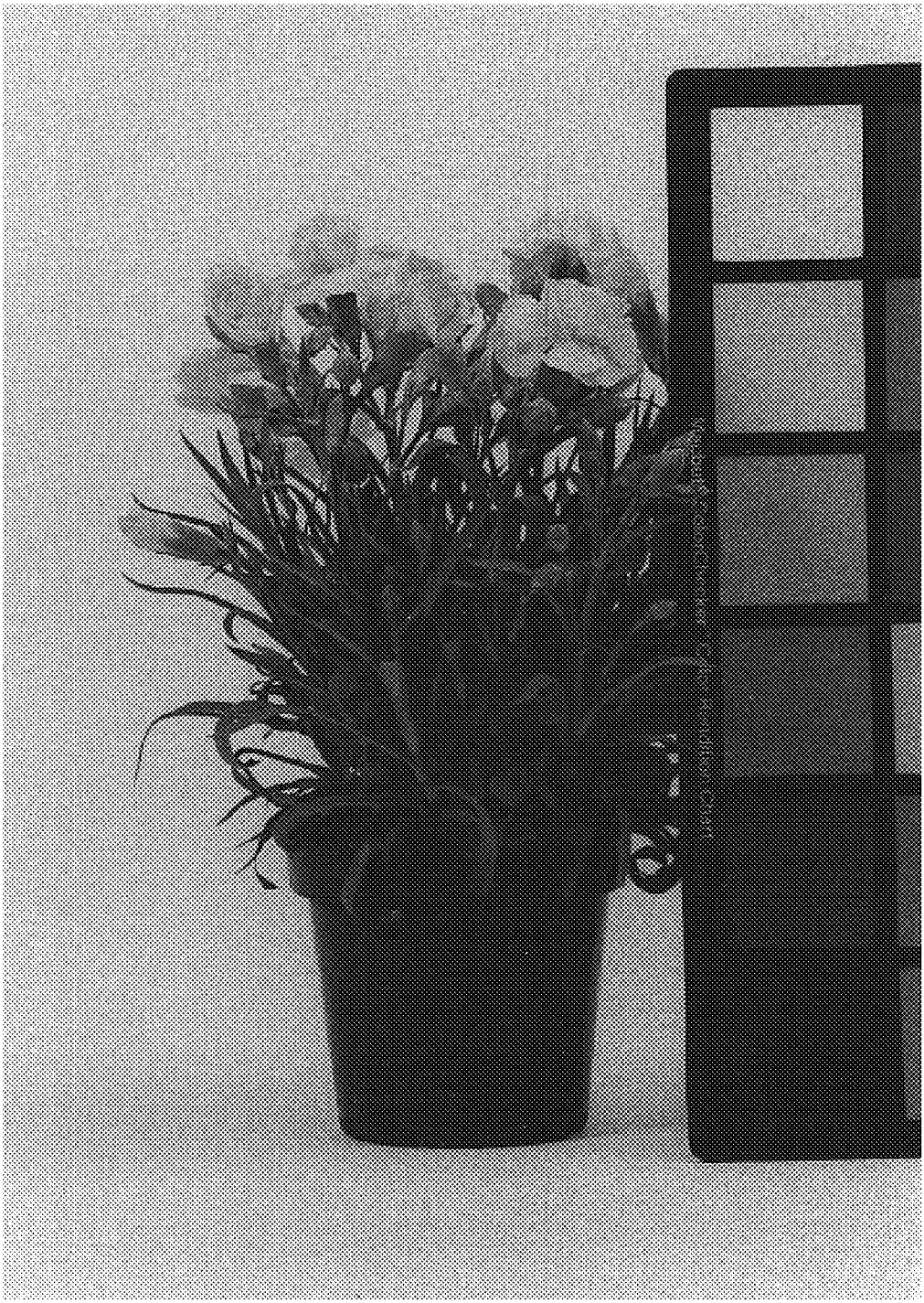

* * * * *